United States Patent [19]
Friedman et al.

[11] Patent Number: 5,811,129
[45] Date of Patent: *Sep. 22, 1998

[54] HYDROXYLATED MILK GLYCERIDES

[75] Inventors: Amnon Friedman, Marlboro; Stuart Barry Polovsky, Matawan; Joseph Peter Pavlichko, Helmetta; Luis Sabino Moral, East Brunswick, all of N.J.

[73] Assignee: Amerchol Corporation, Edison, N.J.

[ * ] Notice: The term of this patent shall not extend beyond the expiration date of Pat. No. 5,576,027.

[21] Appl. No.: 752,049

[22] Filed: Nov. 19, 1996

Related U.S. Application Data

[63] Continuation-in-part of Ser. No. 279,450, Jul. 25, 1994, Pat. No. 5,576,027, which is a continuation-in-part of Ser. No. 905,379, Jun. 29, 1992, abandoned.

[51] Int. Cl.$^6$ ...................................................... A61K 7/48
[52] U.S. Cl. ........................ 424/535; 514/529; 514/546; 514/844; 514/846; 514/873; 554/213
[58] Field of Search .................................... 514/529, 546, 514/844, 846, 873; 554/213; 424/535

[56] References Cited

U.S. PATENT DOCUMENTS

| | | | |
|---|---|---|---|
| 1,994,992 | 12/1935 | Haas et al. | 260/16 |
| 2,443,280 | 5/1948 | Swern et al. | 260/406 |
| 2,485,160 | 10/1949 | Niederhauser et al. | 260/242 |
| 2,688,031 | 4/1954 | Logan | 260/406 |
| 4,126,702 | 11/1978 | Vanlerberghe et al. | 424/365 |

FOREIGN PATENT DOCUMENTS

| | | |
|---|---|---|
| 0135018 | 3/1985 | European Pat. Off. . |
| 0257510 | 3/1988 | European Pat. Off. . |
| 0463668 | 1/1992 | European Pat. Off. . |
| 1793524 | 1/1972 | Germany . |
| 3842191A1 | 6/1990 | Germany . |
| 51011/22 | 2/1980 | Israel . |
| 70001919 | 1/1970 | Japan . |

OTHER PUBLICATIONS

I. Rosenthal, *Milk and Dairy Products,* pp. 12 and 193, VCH (1991).

U. Delbene, "Cosmetic Butter Oil –New Developments and Recent Derivatives". *Cosmetics and Toiletries,* (Jan. 1989).

M. Hudlicky, "Oxidation in Organic Chemistry", *ACS Monograph* 186, (1990).

International Journal of Cosmetic Science 13, 169–190 (1991) "Novel quaternary ammonium salts derived from triglycerides and their application in skin and hair products" Ahmet baydar and Richard Johnston.

Chemistry and Industry, 21 Oct. 1972, "Fatty acid and triglyceride compositions of Shorea Robusta fat: occurrence of cis–9,10–epoxystearic acid and threo–9,10–dihydroxystearic acid" N.V. Bringi and F.B. Padley and R.E. Timms.

*Primary Examiner*—Evelyn Huang
*Attorney, Agent, or Firm*—W. K. Volles

[57] ABSTRACT

Hydroxylated milk glycerides having low levels of ethylenic unsaturation are disclosed. The hydroxylated milk glycerides can have enhanced resistance to rancidification and as such, are suitable for use in personal care compositions e.g., lotions, skin creams, lipsticks, eye shadow, and makeup. Personal care compositions comprising the hydroxylated milk glycerides can have enhanced properties as compared to personal care compositions which do not comprise the hydroxylated milk glycerides or alternatively comprise milk fat.

26 Claims, No Drawings

HYDROXYLATED MILK GLYCERIDES

CROSS REFERENCE TO RELATED APPLICATION

This application is a continuation-in-part of Ser. No. 279450 U.S. Pat. No. 5,576,027, issued Nov. 19, 1996, which is a continuation-in-part of Ser. No. 07/905,379, filed Jun. 29, 1992, now abandoned.

FIELD OF THE INVENTION

The present invention relates to milk glycerides and, more specifically, to hydroxylated milk glycerides useful, for example, in personal care compositions.

BACKGROUND OF THE INVENTION

Milk fat (also commonly known as butter fat or butter oil) comprises the oily portions of the milk of mammals. Cow's milk, which is a common source of milk fat, contains approximately four weight percent milk fat. Milk fat is comprised primarily of triglycerides, e.g., about 98 weight percent, although some diglycerides and monoglycerides may also be present. The fatty acids from the glycerides in milk fat typically contain from 4 to 18 carbon atoms. In addition, typically about 30 to 40 weight percent of the fatty acids are unsaturated, i.e., contain one or more double bonds.

Low-fat and skim milk-based products are made by removing milk fat from whole milk. As a result of the high commercial demand for low-fat and skim milk-based products, there is currently a large supply of milk fat which is available for other uses.

Various components of milk have been proposed for use in personal care compositions. For example, the protein fractions of milk are known to have the ability to hydrate skin and help retain water. Whey proteins are known to have good gelling properties. Casein is often used in personal care compositions for its emulsification and foaming properties. Even whole milk is used to enhance the cleansing effect of surfactants in personal care compositions.

The use of milk fat also has been proposed in personal care compositions. However, the use of milk fat in personal care compositions has been limited due to problems with rancidity which can cause off-color, offensive odor and poor taste in the personal care compositions such as, for example, in lipsticks.

The rancidification of milk fat is dependent on the action of two kinds of chemical transformation: lipolysis and autoxidation. Lipolysis is the process of enzymatic hydrolysis of glyceride esters and is associated in dairy products with the appearance of rancid flavor due to the accumulation of free fatty acids. Lipases are the enzymes capable of catalyzing this hydrolysis and are often dormant until stimulated by a change in the milk, such as dilution, mechanical, thermal or chemical reaction. The enzyme activity can be decreased by the use of small amounts of salt and by pasteurization treatment. Ultraviolet and gamma ionizing radiations also deactivate lipase by chemical modification of the enzyme. Autoxidation occurs by a free-radical chain mechanism which includes initiation, propagation and termination, resulting in the formation of hydroperoxides which can collapse to stable carbonyl and hydroxy compounds, or react with other components in the personal care composition.

In view of the current commercial availability of milk fat, new modified milk-fat products are desired which can provide increased resistance to rancidification. Such milk-fat products could be used, for example, in a variety of personal care compositions.

SUMMARY OF THE INVENTION

By the present invention, hydroxylated milk glycerides, preferably hydroxylated derivatives of milk fat triglycerides, are provided which can have enhanced resistance to rancidity, as compared to untreated milk fat. As such, the hydroxylated milk glycerides of the present invention are suitable for use in personal care compositions, such as, for example, lotions, skin creams, make-ups, lipsticks, eye shadows and conditioning agents for hair care.

DETAILED DESCRIPTION OF THE INVENTION

The raw material suitable for use in accordance with the present invention is milk fat. Milk fat is typically obtained from the manufacture of butter or the skimming process of milk. In general, milk fat is isolated from the cream fraction of milk by methods involving centrifugation, phase inversion, heating and drying. Milk fat can also be isolated from butter by heating the butter which causes it to separate into a fat fraction and a serum fraction. Further details concerning the isolation of milk fat from milk and butter are known in the art. Milk fat is commercially available from a variety of sources, such as, for example, Land Of Lakes, Inc., Arden Hills, Minn.

Generally, milk fat is comprised of glycerides, primarily triglycerides, e.g., greater than 95 weight percent triglycerides. Hydrolysis of the milk fat is commonly employed to characterize the product. Details concerning the hydrolysis of milk fat are known to those skilled in the art. Upon hydrolysis, the milk fat yields glycerol and a fatty acid portion typically comprising (a) from about 1 to 10 weight percent of fatty acids containing 4 to 8 carbon atoms; (b) from about 5 to 30 weight percent of fatty acids containing from 9 to 14 carbon atoms; and (c) from about 60 to 94 weight percent of fatty acids containing about 15 to 20 carbon atoms. Thus, as used herein, the reference to fatty acids means the fatty acids that result from the hydrolysis of the glycerides in the milk fat in addition to any free fatty acids which may be present. Typical fatty acids in the 4 to 8 carbon atom range include butyric acid, caproic acid, and caprylic acid. Typical fatty acids in the 9 to 14 carbon atom range include capric acid, lauric acid and myristic acid. Typical fatty acids in the 15 to 20 carbon atom range include palmitic acid, palmitoleic acid, stearic acid, oleic acid, linoleic acid and linolenic acid.

Since the hydrolysis of milk fat produces fatty acids, which are not very volatile, characterization in analytical equipment such as gas/liquid chromatographs can be difficult. Accordingly, an alternative technique to hydrolysis which provides the same characterization is to saponify the milk fat, e.g., with methanolic sodium hydroxide, and then esterify the product, e.g., with methanolic boron trifluoride, to provide methyl esters of the corresponding fatty acids which can then be readily analyzed. Further details concerning the saponification and characterization of milk fat are known to those skilled in the art.

Often, about 30 to 40 weight percent of the fatty acids in milk fat is unsaturated, i.e., contains one or more double bonds. Most, if not all, of the unsaturated fatty acids are in the 15 to 20 carbon atom range, e.g., palmitoleic acid, oleic acid, linoleic acid and linolenic acid. Levels of unsaturation in fatty acids, such as contained in milk fat, are generally measured by determining the Iodine Value. The Iodine Value is a measure of the degree of unsaturation and is expressed as grams of iodine absorbed per 100 grams of the material. The procedure for determining Iodine Value is known in the art and described, for example, in Analytical Test Methods, Test No. AATM 112-2, Amerchol Corporation, issued Mar. 1, 1978. Typical Iodine Values for the milk fat raw material used in the present invention exceed 25 and often range from about 30 to 40. Another parameter often used to characterize the level of unsaturation is known as the "moles of ethylenic unsaturation". The moles of ethylenic unsaturation are determined by dividing the Iodine Value by the molecular weight of molecular iodine, i.e. 253.8 grams per gram mole, which yields moles of ethylenic unsaturation per mole of iodine per 100 grams of material. Typically, the milk fat will have greater than 0.10 moles of ethylenic unsaturation (per 100 grams of milk fat).

In addition, the milk fat will typically have a Saponification Value of at least about 210 and typically from about 215 to 245, although lower and higher values are within the scope of the invention. The Saponification Value is a measure of the free acid and saponifiable ester groups. It is expressed as the number of milligrams of potassium hydroxide required to neutralize the free acids and saponify the esters contained in one gram of the milk fat. Methods for determining Saponification Value are known in the art and described for example, in Analytical Test Methods, Test Number AATM 110-1 Amerchol Corporation, issued Jun. 1, 1989.

The hydroxylated milk glycerides of the present invention are prepared by hydroxylating the milk fat raw material. In general, the milk fat is contacted with an organic per-acid which yields an epoxide ring, also known as oxirane ring, across the former double bond. The resulting epoxides are further reacted, either in the epoxidation medium by continuing the reaction or they are isolated and separately reacted in a second step, to hydroxylate at least a portion of the epoxides. The resulting compound is a hydroxy ester or a dihydroxy (1,2-diol) glyceride. The epoxidation step is generally conducted at a temperature from about 40° to 60° C. The hydroxylation step is generally conducted at a temperature from about 60° to 90° C. When the hydroxylation step is conducted by continuing the reaction in the epoxidation medium, the temperature is preferably increased from about 40° to 60° C. to about 60° to 90° C. when the epoxidation reaction is at or near completion. Further details concerning oxidation and hydroxylation are known in the art and disclosed, for example, by M. Hudlicky, "Oxidations in Organic Chemistry", *ACS Monograph* 186, American Chemical Society (1990).

As with the milk fat raw material, upon hydrolysis the hydroxylated milk glyceride prepared in accordance with the present invention yields glycerol and a fatty acid portion typically comprising: a) from about 1 to 10 weight percent of fatty acids containing from 4 to 8 carbon atoms; b) from about 5 to 30 weight percent of fatty acids containing from 9 to 14 carbon atoms; and c) from about 60 to 94 weight percent of fatty acids containing from 15 to 20 carbon atoms. Preferably, the fatty acids containing 4 to 8 carbon atoms are selected from the group consisting of butyric acid, caproic acid, caprylic acid and mixtures thereof; the fatty acids containing 9 to 14 carbon atoms are selected from the group consisting of capric acid, lauric acid, myristic acid and mixtures thereof; and the fatty acids containing 15 to 20 carbon atoms are selected from the group consisting of palmitic acid, stearic acid and the epoxidized or hydroxylated reaction products of palmitoleic acid, oleic acid, linoleic acid, linolenic acid and mixtures thereof. In addition, like milk fat, the hydroxylated milk glyceride of the present invention is preferably comprised of at least about 95 weight percent triglycerides and more preferably at least about 98% triglycerides, with the balance comprising monoglycerides and diglycerides.

However, unlike milk fat, the hydroxylated milk glyceride of the present invention will have a reduced degree of unsaturation. Typically, the hydroxylated milk glyceride will have less than about 0.1 moles of ethylenic unsaturation, preferably less than 0.05 moles of ethylenic unsaturation and, most preferably, less than 0.01 moles of ethylenic unsaturation. Similarly the Iodine Value of the hydroxylated milk glycerides will be reduced as compared to milk fat. Preferably, the Iodine Value will be less than 10, more preferably less than 5, and most preferably between about 0.1 and 2.0.

As a result of the hydroxylation procedure, at least 10 percent of the fatty acids in the hydroxylated milk fat will contain hydroxyl groups. Preferably, most, if not all of such hydroxyl groups will be present in the fatty acid portion having 15 to 20 carbon atoms. Preferably, at least about 25 weight percent and more preferably at least about 40 weight percent of the fatty acids containing about 15 to 20 carbon atoms will contain hydroxyl groups. Hence, if for example, 70% of the fatty acids in the hydroxylated milk glyceride contain about 15 to 20 carbon atoms, then at least about 7 weight percent of the total fatty acid content will contain hydroxyl groups if 10 weight percent in the 15–20 carbon range contain hydroxyl groups. Moreover, it is preferred that the hydroxyl content be effective to inhibit rancidification of the hydroxylated milk glyceride when stored at from about 15° to 30° C. for at least 1 month, and more preferably, for at least one year. Preferably the Hydroxyl Value of the hydroxylated milk glyceride will be greater than 10, more preferably greater than 15, even more preferably greater than 20, and most preferably between about 20 and 80. The Hydroxyl Value is a parameter commonly used to characterize the number of hydroxyl groups present on the fatty acid. The Hydroxyl Value is defined as the number of milligrams of potassium hydroxide necessary to neutralize acetic acid which results from acetylation of one gram of material. Methods for determining Hydroxyl Value are known in the art and described, for example, in Analytical Test Methods, Test No. AATM 111A-1, Amerchol Corporation, issued Mar. 1, 1978.

Preferably, the hydroxylated milk glycerides of the present invention have an equivalent weight of from about 210 to 270 milligrams per milliequivalent (mg/meq). The equivalent weight can be readily calculated from the Saponification Value by dividing the milliequivalent weight of potassium hydroxide (56,100) by the Saponification Value. The molecular weight can then be calculated by multiplying the equivalent weight by three since there are three ester linkages per molecule of triglyceride. Preferably the molecular weight is from about 600 to 810 grams per gram mole. Further details concerning the determination of the equivalent weight and molecular weight are known to those skilled in the art.

Preferably, the hydroxylated milk glycerides of the present invention comprise from about 60 to 90 weight percent carbon, from about 5 to 20 weight percent hydrogen and from about 5 to 20 weight percent oxygen. Often, the hydroxylated milk glyceride will comprise from about 70 to 80 weight percent carbon, to about 10 to 15 weight percent hydrogen and from about 10 to 15 weight percent oxygen. One suitable method for determining the concentration of carbon, hydrogen and oxygen is by elemental analysis the details of which are known to those skilled in the art.

Quite surprisingly, in accordance with the present invention, it has been found that the presence of some epoxide groups, i.e., oxirane rings, in combination with the hydroxyl groups can impart beneficial properties to the hydroxylated milk glycerides, particularly when used in personal care compositions. The amount of epoxide groups present in the hydroxylated milk glyceride will depend on the desired properties of the end use composition. Hence, the properties of the hydroxylated milk glyceride can be tailored to meet the requirements of the end use product, e.g., personal care composition, in question. The adjustment of the ratio of hydroxyl groups to epoxide groups can be readily made by controlling the extent of the hydroxylation reaction during the preparation procedure.

In accordance with the present invention, at least a portion of the fatty acids containing from 15 to 20 carbon atoms will preferably contain epoxide groups. Generally, the molar ratio of hydroxyl groups to epoxide groups will preferably be at least 2:1 and more preferably be at least 4:1. However, occasionally the molar ratio of hydroxyl groups to epoxide groups will preferably be less than 2:1 and more preferably less than 1:1. A parameter generally used to characterize the epoxide content of fatty acids is the Epoxide Value which is calculated by determining the percent oxirane oxygen and multiplying the percent oxirane oxygen by 35.1. The value of 35.1 is determined by dividing the equivalent weight of potassium hydroxide, i.e., 56.1 grams per gram mole, by the equivalent weight of oxygen, i.e., 16 grams per gram mole, and multiplying by 10 (1000/100). The Epoxide Value is expressed as milligrams of potassium hydroxide per gram of material. The percent oxirane oxygen is determined by titrating the oxygen with hydrogen bromide in acetic acid. This test is known in the art and described, for example, in Sampling and Analysis of Commercial Fats and Oils, A.O.C.S. Official Method C.d 9-57 (1988). Typically, the hydroxylated milk glycerides will have an Epoxide Value greater than one and preferably greater than about 10. Preferably, the ratio of Hydroxyl Value to Epoxide Value will be from about 0.05:1 to 30:1 and more preferably from about 0.2:1 to 20:1.

Preferably the hydroxylated milk glycerides of the present invention will have a melting point of less than about 60° C., preferably from about 20° to 50° and more preferably from about 25° to 40° C.

In addition to the hydroxylated milk glycerides, the present invention also includes derivatives of the hydroxylated milk glycerides. Such derivatives can be prepared, for example, by acetylating, ethoxylating, propoxylating, esterifying, transesterifying, saponifying, fractionating, quaternizing, sulfonating, sulfating or sylylating the hydroxylated milk glyceride. Methods for preparing such derivatives are known in the art. Furthermore such derivatives may be prepared using the milk fat raw material, the epoxidized glyceride or the hydroxylated glyceride.

The hydroxylated milk glycerides of the present invention are particularly useful as ingredients in personal care compositions, such as, for example, compositions for the retention of oils, perfumes, emollients, and the like; hair and skin compositions including lotions, creams, make-ups, lipsticks, eye shadows, soaps, cleansers, sun screens, shampoos, rinses, conditioners, anti-dandruff aids; carriers for active agents; and dispersants.

Without wishing to be bound to any particular theory, it is believed that the presence of the low molecular weight fatty acids, i.e., in the $C_4$ to $C_8$ carbon range and in the $C_9$ to $C_{14}$ carbon range, in the hydroxylated milk glycerides substantially contribute to the enhancement of desirable personal care attributes, such as, after- feel, dispersibility, emolliency, emulsifiability, gloss, lubricity, moisturizing ability, smoothness, emulsion stability, rub-in, pigment wetting and viscosity. In contrast, it is believed that the use of high molecular weight fatty acids, e.g., oleic acid, in personal care compositions without the presence of the above lower molecular weight fatty acids would not provide the same degree of enhancement in the above properties. Thus, it is believed that personal care compositions comprising oils based on lard, tallow, coconut, soya bean, peanut, safflower, cottonseed or corn would not have the appropriate distribution of fatty acids, i.e., including the low molecular weight fatty acids which are uniquely present in milk fat, to provide the beneficial properties of the personal care compositions of the present invention.

In general, the amount of the hydroxylated milk glyceride, or derivative thereof, present in the personal care compositions will range from about 0.1 to 99 weight percent. The specific concentration will, of course, depend upon the particular end use composition. Preferably, however, the personal care composition comprises from about 0.1 to 20 weight percent of the hydroxylated milk glyceride. Furthermore, it is preferred that the hydroxylated milk glyceride be present in the personal care composition in an amount effective to enhance at least one of the following properties of the composition; after-feel, dispersability, emolliency, emulsifiability, gloss, lubricity, moisturizing ability, smoothness, emulsion stability, rub-in, pigment wetting and viscosity. In addition to the concentration of the hydroxylated milk glyceride, the ratio of hydroxyl groups to epoxide groups is preferably adjusted in accordance with the present invention to enhance at least one of the above-described properties.

The balance of the personal care composition comprises a suitable carrier, or mixtures of carriers, which acts as a fluid vehicle for the composition. The balance of the composition can be the carrier either alone or in combination with suitable, optional ingredients. The type of carrier is not critical and may be selected from any carrier suitable to the particular end use composition. Illustrative carriers include, for example: water, such as deionized or distilled water; emulsions, such as oil-in-water or water-in-oil emulsions; alcohols, such as ethanol, isopropanol or the like; glycols, such as propylene glycol, glycerine or the like; and combinations thereof. Preferred carriers include water-in-oil or oil-in-water emulsions, water, ethanol and aqueous ethanol mixtures.

Optional ingredients or additives which may be added to the composition can be selected from any suitable substance which may be used for personal care compositions, such as, for example, surfactants, cleansing oils, moisturizers, preservatives, conditioners, pH adjustors, emulsifiers, propellants, reducing agents and thickeners.

Illustrative surfactants include: anionics including soaps or salts of fatty acids, alkyl sulfates, alkyl ether sulfates, alpha-olefin sulfonates, alkyl aryl sulfonates, sarcosinates, alkyl glucose esters or their alkoxylates and in particular sodium lauryl sulfate, ammonium lauryl sulfate, triethanolamine lauryl sulfate, sodium laureth sulfate, isethionates, triethanolamine stearate; nonionics including methyl glucose stearates or their ethoxylates, alkyl polyglucosides, and glycerol monostearate, fatty acid alkanol amides, alkyl aryl polyglycol ether, polyglycol ethers and in particular cocoyl diethanolamide, nonoxynol-7 and octoxynol-9; cationics including alkyl trimethyl ammonium salts, quaternized amides of ethylene diamine, alkyl pyridinium salts and in particular cetrimonium chloride, stearalkonium chloride and cetyl pyridinium chloride; and amphoterics including alkyl β-aminopropionates, betaines, alkyl imidazolines and in particular cocamidopropyl betaine and caproam phocarboxy propionate; and polymeric cationics such as polyquaternium-10 or polyquaternium-24. Illustrative cleansing oils or the like include natural oils, alcohols and branched chain alkyl esters, and in particular, mineral oil, lanolin oil, jojoba oil, sesame oil, ethanol, isopropanol and octyl isononanoate. Illustrative colorants include pigments, dyes, and in particular FD&C Blue No. 1, FD&C No. 1 Aluminum Lake or similar sets of green, red or yellow. Illustrative preservatives may include alcohols, aldehydes, methylchloroisothiazolinone and methylisothiazolinone, p-hydroxybenzoates and in particular methylparaben, propylparaben, glutaraldehyde and ethyl alcohol. Illustrative moisturizers include 2-pyrrolidone-5-carboxylic acid and its salts and esters, alkyl glucose alkoxylates or their esters, fatty alcohols, fatty esters, glycols and, in particular, methyl glucose ethoxylates or propoxylates and their stearate esters, isopropyl myristate, lanolin or cetyl alcohols, aloe, silicones, propylene glycol, glycerol and sorbitol. Illustrative conditioners include stearalkonium chloride, dicetyldimonium chloride, lauryl methyl gluceth-10 hydroxypropyldimonium chloride, and polymeric cationics such as polyquaternium-10, polyquaternium-24 and chitosan and derivatives thereof. Illustrative pH adjustors include inorganic and organic acids and bases and in particular aqueous ammonia, citric acid, phosphoric acid, acetic acid, triethanolamine and sodium hydroxide. Illustrative emulsifiers include anionic and non-ionic surfactants and in particular stearic acid, glycerol monostearate, cocyl diethanolamide, and the particular anionic and nonionic surfactants listed previously. Illustrative propellants include hydrocarbons, fluorocarbons, ethers, carbon dioxide, nitrogen and dimethyl ether. Illustrative reducing agents include ammonium thioglycolate, hydroquinone and sodium thioglycolate. Illustrative thickeners include salts and cellulosics and in particular sodium chloride, water soluble cellulose derivatives such as hydroxyethyl cellulose, associative thickening polymers, acrylates/C10–30 alkyl acrylate cross polymers and water-soluble vinyl polymers, e.g., carbomer.

Other typical ingredients include, for example, one or more of the following: fragrances; foaming agents; sunscreen and suntan agents; depilatory agents; flavors; astringent agents; antiseptics; deodorants; antiperspirants; insect repellants; bleaches and lighteners; anti-dandruff agents; adhesives; polishes; strengtheners; fillers; and barrier materials.

The amount of optional ingredients contained in the composition is not critical and will vary depending upon the particular ingredient, composition and desired use level. The amount of optional ingredients effective for achieving the desired property provided by such ingredients can be readily determined by one skilled in the art.

EXAMPLES

The following examples are provided for illustrative purposes and are not intended to limit the scope of the claims which follow.

The following commercially available products were used in the examples.

Promulgen® D—a mixture of cetearyl alcohol and ceteareth-20, available from Amerchol Corporation, Edison, N.J.

Amerchol L-101®—a mixture of mineral oil and lanolin oil, available from Amerchol Corporation, Edison, N.J.

Carbopol 934—a water-soluble vinyl polymer, available from B. F. Goodrich Company, Brecksville, Ohio Carbopol 940—a water-soluble vinyl polymer, available from B. F. Goodrich Company, Brecksville, Ohio Germaben® II—a mixture of propylene glycol, diazolidinyl urea, methylparaben and propylparaben available from Sutton Laboratories, Inc., Chatham, N.J.

Glucam® E-10—methyl gluceth-10, available from Amerchol Corporation, Edison, N.J.

Amerlate® P—isopropyl lanolate, available from Amerchol Corporation, Edison, N.J.

OHlan® —hydroxylated lanolin, available from Amerchol Corporation, Edison, N.J.

Pigments—iron oxide beige, available from Tricon Colors, Elmwood Park, N.J.

Propal—isopropyl palmitate, available from Amerchol Corporation, Edison, N.J.

Beeswax USP—beeswax, available from Strahl & Pitsch, Inc., West Babylon, N.Y.

Candelilla Wax—candelilla wax, available from Strahl & Pitsch, Inc., West Babylon, N.Y.

Carnuba Wax—carnuba wax, available from Strahl & Pitsch, Inc., West Babylon, N.Y.

Ozokerite—ozokerite, available from Strahl & Pitsch, Inc., West Babylon, N.Y.

Glucam® P-20—PPG-20 methyl glucose ether, available from Amerchol Corporation, Edison, N.J.

Glucam® E-20—methyl gluceth-20, available from Amerchol Corporation, Edison, N.J.

Example 1

Process For Preparing Hydroxylated Milk Glyceride

Approximately 800 grams of milk fat having a Saponification Value of 229.0, an Epoxide Value of 0.35, a Hydroxyl Value of 3.14 and an Iodine Value of 35.1, obtained from Land O'Lakes, Inc. of Arden Hills, Minn., were heated to about 40° C. and poured into 160 grams of heptane. The solution was stirred for one-half hour and the temperature was maintained between 35° and 40° C. About 45 grams of acetic acid were added to this mixture followed by 6.8 grams of a 50 percent aqueous solution of sulfuric acid. About 130 grams of a 50 percent aqueous hydrogen peroxide solution were added in small increments to the mixture over one hour. The temperature was then increased to about 57° to 60° C. and stirred for six hours. The stirring was then stopped and the solution was allowed to settle. A lower aqueous layer and an upper heptane layer were formed. The lower aqueous layer was removed and the upper heptane layer was washed three times with hot water having a temperature of about 60° C. The washed heptane layer was then neutralized with a 45% aqueous potassium hydroxide solution to a pH of about 5 to 7. The heptane was then removed by distillation under vacuum and the reaction product was dried under vacuum at 100° C. The dried product was then steam-deodorized under vacuum conditions and filtered at about 50° to 60° C. using diatomaceous earth. Approximately 795 grams of a white waxy product was recovered and had a Hydroxyl Value of 11.4, an Iodine Value of 0.99, a Saponification Value of 225.4 and an Epoxide Value of 62.4. The product had approximately 0.004 moles of ethylenic unsaturation.

Example 2

Process For Preparing Hydroxylated Milk Glyceride

To a 2,000 gallon reactor, 4,896 pounds of milk fat (obtained from Land O'Lakes, Inc., Arden Hills, Minn.)

were added having a Saponification Value of 229.0, an Epoxide Value of 0.35, a Hydroxyl Value of 3.14 and Iodine Value of 35.1, or 138 millimoles of ethylenic unsaturation per 100 grams. The milk fat was heated to about 40° C. Then, 980 pounds of heptane were poured in. The solution was stirred for one-half hour while the temperature was maintained between 35° and 40° C. About 765 pounds of acetic acid were added to this mixture followed by 46 pounds of 52.6 weight % aqueous solution of sulfuric acid. Over a one-hour period at 45°–50° C., 765 pounds of a 50 weight % aqueous hydrogen peroxide solution were added to the mixture in small increments. The temperature was increased to about 58° to 60° C. and stirred for six hours.

The stirring was then stopped and the solution was allowed to settle. A lower aqueous layer and an upper heptane layer formed. The lower aqueous layer was removed and the upper heptane layer was washed four times with hot water (approx. 60° C.). The washed heptane layer was then neutralized with a 45 weight % aqueous potassium hydroxide solution to a pH of about 6. The heptane was then removed by distillation under vacuum and the reaction product was dried under vacuum at 100° C. The dried product was steam deodorized under vacuum conditions for three hours, neutralized again to pH 6 and filtered at about 50° to 60° C. using diatimaceous earth. This yielded 4753 pounds of a white, waxy product with a Hydroxyl Value of 40.1, Iodine Value of 0.93, Saponification Value of 226.97 and an Epoxide Value of 25.35. The product has approximately 3.6 millimoles of ethylenic unsaturation/100 grams of material.

Example 3

Rancidity Test

A 50 gram sample of the raw material milk fat referred to in Example 1, a 50 gram sample of the hydroxylated milk glyceride prepared in Example 1 and a 50 gram sample of the hydroxylated milk glyceride prepared in Example 2 were placed in an oven maintained at about 45° C. After about 30 days the milk fat sample had an offensive odor which is characteristic of rancidification. The milk fat sample was accordingly unsuitable for use in a personal care composition. After 2 months, the hydroxylated milk glyceride samples were removed from the oven. The hydroxylated milk glyceride samples had no offensive odor and, thus, would be suitable for use in personal care compositions.

Example 4

Characterization of Milk Fat

A sample of 0.12 to 0.14 gm of milk fat such as described with reference to Example 1 is placed in a small reactor vial. To this is added 4 milliliters of a 0.5N NaOH solution in methanol. The mixture is stirred and heated to 60° C. to complete the saponification. The temperature is maintained at 60° C. for 10 minutes after which it is allowed to cool to room temperature.

To this is added 5 milliliters of a 14 weight % solution of $BF_3$ in methanol. The total material is then heated to 60° C. and kept there for 10 minutes to produce the methyl esters. of the fatty acids. After allowing this to cool to room temperature, the mixture is stirred with 5 mililiters of hexane at 60° C. for 3 minutes in order to extract the methyl esters.

The cooled hexane solution is washed in a separatory funnel with 20 mililiters of a saturated NaCl solution and then dried over anhydrous sodium sulfate for 2 hours.

The methyl esters are then analyzed by gas/liquid chromatography, the details of which are known to those skilled in the art.

The same characterization can be made on the hydroxylated milk fat derivatives.

Example 5

Properties of Milk Fat and Hydroxylated Milk Glyceride Samples

Three hydroxylated milk glyceride samples were prepared generally following the procedure set forth in Example 1. The Epoxide Value, Hydroxyl Value, Iodine Value and Melting Point of each sample are listed in Table 1. Also included are the values for a sample of raw material milk fat, as well as the values for a sample prepared as in Example 2 (Sample VIII).

TABLE 1

| | Parameter | | | |
|---|---|---|---|---|
| Sample | Epoxide Value | Hydroxyl Value | Iodine Value | Melting Point, °C. |
| I | 49 | 10.7 | 8.9 | 26.8 |
| II | 62.5 | 12.0 | 2.7 | 31.0 |
| III | 62.8 | 14.0 | 0.5 | 24.6 |
| Milk Fat IV | — | 2.1 | 34.8 | 30.8 |
| VIII | 25.4 | 40.1 | 0.93 | — |

Samples I to III and the Milk Fat Sample had the following fatty acid compositions as set forth below in Table 2.

TABLE 2

| | Concentration, Area Percent* | | | |
|---|---|---|---|---|
| Fatty Acid | Sample I | Sample II | Sample III | Milk Fat Sample IV |
| Butyric | 2.8 | 2.4 | 2.1 | 3.8 |
| Caproic | 2.2 | 1.8 | 3.0 | 2.3 |
| Caprylic | 1.2 | 1.2 | 1.2 | 1.3 |
| Capric | 2.6 | 2.5 | 3.0 | 3.2 |
| Lauric | 3.1 | 3.3 | 3.7 | 3.4 |
| Myristic | 10.3 | 11.2 | 12.3 | 11.2 |
| Myristoleic | 0.2 | | | 1.2 |
| Palmitic | 27.2 | 30.3 | 32.1 | 29.7 |
| Palmitoleic | 0.3 | | | 1.2 |
| Stearic | 20.7 | 17.1 | 13.9 | 13.5 |
| Oleic | 5.5 | | | 25.8 |
| Linoleic | 0.1 | | | 2.8 |
| Linolenic | 0.1 | | | 0.6 |
| Others** | 24.2 | 30.2 | 29.8 | — |

*Determined by gas/liquid chromatography
**Believed to be the hydroxylated or epoxidized reaction product of palmitoleic acid, oleic acid, linoleic acid, linolenic acid and mixtures thereof.

Example 6

Characterization of Samples

In order to further characterize the hydroxylated milk glycerides of the present invention, four samples were prepared. Control Sample V was a hydrogenated milk fat prepared by following the procedure described in Japanese Patent Application Number 540-24867, published Jan. 22, 1970. Milk fat Sample VI was substantially the same as Milk fat Samples IV and was used to prepare all of the derivatives used in this example. Sample VII was an epoxidized milk glyceride prepared by following the procedure of Example 1. Sample VIII was a hydroxylated milk glyceride prepared by following the procedure of Example 2.

TABLE 3

| Sample | Saponifica. Value | Epoxide Value | Hydroxyl Value | Iodine Value |
|---|---|---|---|---|
| V (hydrogenated) | 228.7 | <0.1 | 0.9 | 0.2 |
| VI (milk fat) | 229.2 | <0.1 | 4.1 | 32.7 |
| VII (epoxidized) | 224.9 | 59.2 | 11.5 | 2.7 |
| VIII (hydroxylated) | 227.0 | 25.4 | 40.1 | 0.9 |

The samples were additionally characterized by infrared spectroscopy. The spectrometer used was a model FTS-50 FT-IR spectrometers, available from Bio-Rad, Digilab Division, Cambridge, Mass. 02139. The spectrometer was equipped with a TGS detector. The procedure used was as follows. Some of the sample as received was smeared uniformly on a clean KBr crystal and a transmission spectrum was recorded. Data files were first saved on the hard disk of the spectrometer computer and later onto floppy disks. Fifty scans were co-added and the spectra were recorded at a resolution of 4 reciprocal centimeters.

Absorbance peaks characteristic of hydroxyl groups (OH), epoxide groups

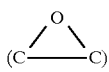

and $CH_2$ groups were absorbed at the wave numbers set forth in Table 4, below.

TABLE 4

| | Absorbance, reciprocal centimeters (cm$^{-1}$) | | | | |
|---|---|---|---|---|---|
| Sample | OH 3533 | OH 3470 | OH 900 | (C—O—C) 838 | $CH_2$ 721 |
| V | 0.0001 | 0.0028 | 0.0164 | 0.0109 | 0.0748 |
| VI | 0.0006 | 0.0034 | 0.0123 | 0.0087 | 0.0436 |
| VII | 0.0027 | 0.0058 | 0.0184 | 0.0151 | 0.0372 |
| VIII | 0.0161 | 0.0169 | 0.0185 | 0.0102 | 0.0312 |

The data in Table 4 demonstrate substantially higher absorbance values for OH groups in Sample VIII (hydroxylated milk fat) than the other samples. The absorbance at 3533 cm$^{-1}$ is believed to be due to non-hydrogen bonded OH groups and the absorbance at 3470 cm$^{-1}$ is believed to be due to hydrogen bonds. Table 5, below, shows the ratio of the absorbance values (areas) for the OH groups as compared to the $CH_2$ groups.

TABLE 5

| Sample | 3533/721 cm$^{-1}$ × 10$^2$ | 3470/721 cm$^{-1}$ × 10$^2$ |
|---|---|---|
| V | 0.13 | 3.74 |
| VI | 1.38 | 7.80 |
| VII | 7.26 | 15.6 |
| VIII | 51.6 | 54.2 |

Preferably, the hydroxylated glycerides of the present invention demonstrate OH group absorbance at a wave number of from about 3300 to 3600 cm$^{-1}$ and $CH_2$ group absorbance at a wave number of from about 710 to 740 cm$^{-1}$. Preferably, the ratio of the absorbance areas of OH group to $CH_2$ group is at least about 10, preferably at least about 30 and more preferably at least about 50.

The samples were also characterized by nuclear magnetic resonance (NMR) spectroscopy. The spectrometer was AM X-300, available from Bruker, Karlsruhe, Germany.

The studies were conducted at ambient temperature using $CDCl_3$ as a solvent. To resolve all relevant resonances, various experiments were performed. One-dimensional $^1H$ spectra were collected from single pulse excitations followed by Fourier transformation. Routine $^{13}C$ spectra were obtained by single pulse excitations combined with $^1H$ decoupling. The $^1H$—$^{13}C$ polarization transfer sequence was DEPT-135, which used the 135° read pulse to identify $CH_2$ groups as negative signals and both CH and $CH_3$ groups as positive signals. Two-dimensional $^1H$ correlations were established by the COSY pulse sequence, which showed off-diagonal peaks for those protons that interacted through direct scalar couplings. The homonuclear connectivities were further extended to the next $^1H$ partners by the relayed COSY experiment. Identities of $^{13}C$ and attached $^1H$ spins were revealed by the two-dimensional pulse sequence leading to correlation maps of heteronuclear chemical shifts.

All samples contributed to a pair of $^{13}C$ NMR signals at 62.1 and 68.9 ppm, which had the integral ratio of 2:1. Therefore, they represented two equivalent $CH_2$ groups and one CH group. The protons in the $CH_2$ group resonated at 4.2 and 4.3 ppm and showed scalar coupling to the proton in the CH group with the chemical shift of 5.3 ppm. Since these protons did not contribute to any additional off-diagonal peaks in the COSY correlation map, they belonged to an isolated network of $^1H$ spins. Based on the coupling pattern and values of chemical shifts, the assignment of the glyceride backbone unambiguously confirmed that all samples contained triglyceride structures.

Although triglycerides were the main component of milk fat, a small amount of diglycerides was also expected in the starting material and derivatives. If the alpha position on the glycerol remained un-esterified, the $CH_2$—OH moiety contributed to $^{13}C$ and $^1H$ signals at 61.2 and 3.7 ppm. If the hydroxyl group was left at the beta position, the CH—OH resonances appeared at 68.0 and 4.1 ppm, respectively. Quantitative results, however, showed that the typical concentration of diglycerides did not exceed approximately 1 wt %. Some hydroxyl groups were present on the glycerol backbone, but they were introduced by the starting material and practically unaffected by the derivatization.

On the other hand, substantial numbers (i.e., up to 7.6 per 100 fatty acids in Sample VIII) of additional hydroxyl groups were formed by the procedure described in this invention, and NMR spectra showed that they were incorporated into moieties —$CH_2$—CH(OH)—CH(OH)—$CH_2$—. The characteristic $^{13}C$ and $^1H$ chemical shifts were: 74.4 and 3.35 ppm for the CH(OH) groups and 33.6 and 1.45 ppm for the neighboring $CH_2$ groups. Since the moiety must be connected to additional carbons on each side, at least 6 carbons were found in a row, thus clearly indicating that these hydroxyl groups were on the fatty acid chains. Therefore, they represented one of the products obtained by derivatization of olefinic bonds.

Obviously, the source should be unsaturated fatty acids, which were abundantly present in milk fat and easily detected by, for instance, $^{13}C$ signals of =CH— groups with chemical shifts between 120 and 135 ppm. If the samples were treated by the procedures described in this invention, all olefinic bonds were eliminated according to NMR results. NMR also showed that Samples VII and VIII differed from the fully hydrogenated milk fat (Sample V), which was simply converted into a triglyceride of saturated fatty acids with the average formula —O—CO—$C_nH_{2n+1}$ where n=13.3.

Besides the formation of hydroxyl groups, the reaction produced epoxy moieties. They were found in two isomers designated as cis and trans. If the two protons were on the same side of the plane determined by the two carbons and oxygen, the isomer was cis and had $^1H$ chemical shift of 2.9 ppm. Similarly, the trans isomer was distinguished by the $^1H$ chemical shift of 2.65 ppm. Quantitative results showed, for instance, that Sample VII contained 28 epoxy moieties per 100 fatty acids.

Epoxy groups can be isomerized into keto groups, and the resulting moiety —$CH_2$—$CH_2$—CO—$CH_2$—$CH_2$— contributed to characteristic resonances. The carbonyl carbon had chemical shift of 211.1 ppm while the first and second neighboring methylenes resonated at 42.8 and 23.9 ppm. $^1H$ chemical shifts of attached protons were 2.37 and 1.55 ppm, respectively.

The data obtained from the NMR work demonstrated that: (i) the structure of the samples was a triglyceride; (ii) substantial numbers of hydroxyl groups were present on the fatty acid portion of the triglyceride for Sample VII and Sample VIII; (iii) Samples V and VI did not have hydroxyl groups on the fatty acid portion; (iv) none of the samples had substantial numbers of hydroxyl groups on the glycerol backbone of the triglyceride; and (v) Sample VII and Sample VIII also had epoxy and keto groups on the fatty acid portion of the triglyceride.

Further details concerning the techniques used in the infared analysis and the nuclear magnetic resonance characterization are known to those skilled in the art.

Example 7

Preparation of Lotion

Five lotion samples, L-1 to L-5, were prepared having the compositions set forth below in Table 6.

TABLE 6

| Lotion | Composition, Weight Percent | | | | |
|---|---|---|---|---|---|
| | L-1 | L-2 | L-3 | L-4 | L-5 |
| Phase A | | | | | |
| Promulgen ®D | 1.75% | 1.75% | 1.75% | 1.75% | 1.75% |
| Mineral Oil, 70 vis. | 15.00 | 15.00 | 15.00 | 15.00 | 15.00 |
| Amerchol L-101 ® | 5.00 | 5.00 | 5.00 | 5.00 | 5.00 |
| Hydroxylated Milk Glyceride (Sample I) | — | — | 0.75 | — | — |
| Hydroxylated Milk Glyceride (Sample II) | 0.75 | — | — | — | — |
| Hydroxylated Milk Glyceride (Sample III) | — | — | — | 0.75 | — |
| Milk Fat Sample | — | 0.75 | — | — | — |
| Phase B | | | | | |
| Deionized Water | 73.50 | 73.50 | 73.50 | 73.50 | 74.25 |
| Carbopol 934 (3% solution) | 1.00 | 1.00 | 1.00 | 1.00 | 1.00 |
| Triethanolamine (99%) (10% solution) | 2.00 | 2.00 | 2.00 | 2.00 | 2.00 |
| Germaben ® II | 1.00 | 1.00 | 1.00 | 1.00 | 1.00 |
| Viscosity, cps | 10,000 | 14,000 | 18,000 | 12,000 | — |
| pH, 250° C. | 7.1 | 7.2 | 7.3 | 7.3 | — |

The above lotions were prepared according to the following procedure. Phase B was prepared by heating a three weight percent aqueous solution of Carbopol 934 to 75° C. and adding to it a ten weight percent solution of triethalanolamine. Then the Germaben® II and the deionizied water were added to the mixture of Carbopol 934 and triethanolamine to form Phase B.

Phase A was prepared by mixing all of the ingredients at a temperature of 75° C. until the mixture was uniform. At this point, Phase B was added to Phase A and mixed at 75° C. for 15 minutes. The lotion was then allowed to cool to room temperature.

Lotion L-5 contained no hydroxylated milk glycerides or milk fat and generally had the following characteristics when applied to the skin: wet application; whitening upon rub-in; and waxy after-feel. Lotion L-2 comprised milk fat and had generally better characteristics than lotion L-5 but also had: wet application; poor spreadability and slippery feel on rub-in; less whitening upon rub-in as compared to L-5; and dry after feel. Lotions L-1, L-3 and L-4 had superior characteristics, as compared to lotions L-2 and L-5, and more specifically had: easier application; only slight whitening; smooth feel on rub-in and silky after feel. The viscosities, which were measured with a Brookfield Viscometer LTV, Spindle T-C at 5 rpm, and the pH values are also set forth in Table 3 above. The viscosities and pH values were suitable for a lotion.

Example 8

Preparation of Skin Cream Four skin creams, C-1 to C-4, were prepared having the compositions set forth below in Table 7.

TABLE 7

| Skin Cream | Composition, Weight Percent | | | |
|---|---|---|---|---|
| | C-1 | C-2 | C-3 | C-4 |
| Phase A | | | | |
| Carbopol 940 | 0.10 | 0.10 | 0.10 | 0.10 |
| Deionized Water | 70.80 | 70.80 | 70.80 | 70.80 |
| Phase B | | | | |
| Deionized Water | 10.00 | 10.00 | 10.00 | 10.00 |
| Triethanolamine (99%) | 0.10 | 0.10 | 0.10 | 0.10 |
| Phase C | | | | |
| Mineral Oil, 70 vis. | 10.00 | 10.00 | 10.00 | 10.00 |
| Promulgen ® D | 3.50 | 3.50 | 3.50 | 3.50 |
| Glucam ® E-10 | 3.00 | 3.00 | 3.00 | 3.00 |
| Germaben ® II | 1.00 | 1.00 | 1.00 | 1.00 |
| Hydroxylated Milk Glyceride (Sample I) | 1.50 | — | — | — |
| Hydroxylated Milk Glyceride (Sample II) | — | 1.50 | — | — |
| Milk Fat Sample | — | — | 1.50 | — |
| Hydroxylated Milk Glyceride (Sample III) | — | — | — | 1.50 |
| Viscosity, cps | 46,000 | 50,000 | 38,000 | 46,000 |
| pH, 25° C. | 7.0 | 6.8 | 6.0 | 7.0 |

The above skin creams were prepared according to the following procedure. Phase A was prepared by mixing the Carbopol 940 with the deionized water and heating slowly to 75° C. Phase B was prepared by mixing the triethanolamine with the deionized water and heating to 75° C. Phase B was then added to Phase A at a temperature of 75° C. Phase C was prepared by mixing the mineral oil Promulgen D, Glucan E-10, Germaben® II and either the hydroxylated milk glyceride or Milk Fat Sample at 75° C. The AB Phase was then added to Phase C and mixed at a temperature of 75° C. for 15 minutes. The skin cream was then allowed to cool to room temperature with mixing.

Skin Cream C-3 contained milk fat and generally had the following characteristics: slightly dull emulsion; grainy with low uniformity; whitening on rub-in; and waxy afterfeel. Skin Creams C-1, C-2 and C-4 generally had superior characteristics to C3, and more specifically, had: whiter, glossier emulsions; more uniform consistency; easier rub-in; and a silky, smooth after feel. The viscosities, which were measured with a Brookfield Viscometer LTV, Spindle T-C at 5 rpm, and the pH values are also set forth in Table 4 above. The viscosities and pH values were suitable for a skin cream.

Example 9

Preparation of Moisturizing Lipsticks

Six moisturizing lipstick formulations L-1 to L-6, were prepared having compositions set forth below in Table 8.

TABLE 8

| Moisturizing Lipsticks | Composition, Weight Percent | | | | | |
|---|---|---|---|---|---|---|
| | LS-1 | LS-2 | LS-3 | LS-4 | LS-5 | LS-6 |
| Pigment Concentrate: | | | | | | |
| Amerlate ® P | 5.0 | 5.0 | — | — | — | — |
| OHlan ® | 3.0 | — | — | — | — | — |
| Pigments (Iron Oxides) | 8.5 | 8.5 | 8.5 | 8.5 | 8.5 | 8.5 |
| Propal | 20.0 | 20.0 | 22.5 | 17.5 | 22.5 | 22.5 |
| Hydroxylated Milk Glyceride (Sample I) | — | 3.0 | 3.0 | — | — | — |
| Hydroxylated Milk Glyceride (Sample II) | — | — | — | — | 3.0 | — |
| Milk Fat Sample | — | — | — | — | — | 3.0 |
| Hydroxylated Milk Glyceride (Sample III) | — | — | — | 8.0 | — | — |
| Base: | | | | | | |
| Beeswax | 10.5 | 10.5 | 10.5 | 10.5 | 10.5 | 10.5 |
| Candelilla Wax | 7.5 | 7.5 | 7.5 | 7.5 | 7.5 | 7.5 |
| Carnauba Wax | 3.5 | 3.5 | 3.5 | 3.5 | 3.5 | 3.5 |
| Ozokerite | 5.5 | 5.5 | 5.5 | 5.5 | 5.5 | 5.5 |
| Castor Oil | 33.5 | 33.5 | 36.0 | 36.0 | 36.0 | 36.0 |
| Glucam P-20 | 3.0 | 3.0 | 3.0 | 3.0 | 3.0 | 3.0 |

The above lipsticks were prepared according to the following procedure. A pigment concentrate was prepared by grinding the Amerlate® P, OHlan, Pigments, Propal, and either the hydroxylated milk glyceride or Milk Fat Sample until a uniform fine dispersion was produced. The base was prepared by combining the Beeswax USP, Candelilla Wax, Carnauba Wax, Ozokerite, Castor Oil and Glucan P-20 and heating to 85° to 90° C. while mixing slowly. Once a clear and uniform mixture was obtained, the pigment concentrate was added and the mixing was continued until the lipstick formulation was uniform and substantially free of air. The lipstick formulation was then poured into molds at about 70° C. and allowed to cool to room temperature.

Lipstick LS-1 did not contain hydroxylated milk glycerides or milk fat and generally had the following characteristics: hard to rub dry; hard to spread. Lipstick L-6 contained milk fat and generally had better characteristics than LS-1, and more specifically had: a wet rub-in; and heavier after feel. Lipsticks L-2, L-3, L-4 and L-5 contained hydroxylated milk glycerides and had generally superior characteristics to Lipsticks L-1 and L-6, and more specifically, had: a dry rub-in; smooth after feel; and uniform coverage.

Example 10

Four samples of foundation liquid makeup, M-1 to M-4, were prepared having the compositions set forth in Table 9.

TABLE 9

| Foundation Liquid Makeup | Composition, Weight Percent | | | |
|---|---|---|---|---|
| | M-1 | M-2 | M-3 | M-4 |
| Phase A | | | | |
| Deionized Water | 62.70% | 62.70% | 62.70% | 62.70% |
| Glucam ® E-20 | 4.00 | 4.00 | 4.00 | 4.00 |
| Phase B | | | | |
| Deionized Water | 8.50 | 8.50 | 8.50 | 8.50 |
| Triethanolamine (99%) | 0.80 | 0.80 | 0.80 | 0.80 |
| Germaben ® II | 1.00 | 1.00 | 1.00 | 1.00 |
| Phase C | | | | |
| Amerchol L-101 ® | 4.00 | 4.00 | 4.00 | 4.00 |
| Stearic Acid | 2.00 | 2.00 | 2.00 | 2.00 |
| Glyceryl Stearate | 1.00 | 1.00 | 1.00 | 1.00 |
| Mineral Oil, 70 vis. | 5.00 | 5.00 | 5.00 | 5.00 |
| Pigments (Iron Oxides) | 8.00 | 8.00 | 8.00 | 8.00 |
| Milk Fat Sample | — | — | — | 3.0 |
| Hydroxylated Milk Glycerides (Sample III) | 3.00 | — | — | — |
| Hydroxylated Milk Glycerides (Sample II) | — | — | 3.00 | — |
| Hydroxylated Milk Glycerides (Sample I) | — | 3.00 | — | — |
| Viscosity, cps | 14,000 | 30,000 | 18,000 | 16,000 |
| pH, 25° C. | 8.0 | 8.0 | 8.0 | 7.9 |

The above makeup compositions were made according to the following procedure. Phase A was prepared by mixing the Glucam E-20 into the deionized water. Phase B was prepared by mixing the triethanolamine and Germaben® II into the deionized water. Phase A and Phase B were then mixed together until uniform and heated to 78° C. Phase C was prepared by combining the Amerchol L-101, stearic acid glyceryl strearate, mineral oil and either the hydroxylated milk glycerides or Milk Fat Sample and heating to 78° C. During the heating step the pigments were added and all of the ingredients in Phase C were mixed. Phase A and Phase B were then added to Phase C and homomixed for one hour at 78° C. The makeup compositions were then allowed to cool to room temperature with mixing.

Makeup M-4 contained milk fat and generally had the following characteristics: wet application and longer rub-in time; poor spreadability; uneven coverage and hard to work onto skin; heavy feel; and poor shading. Makeups M-1, M-2 and M-3, comprised of hydroxylated milk glycerides, and generally had better characteristics than makeup M-4 and more specifically, had: easier application; excellent spreading; more uniform coverage; and dry powder-like after feel. The viscosities, which were measured with a Brookfield Viscometer LTV, Spindle T-C at 5 rpm, and the pH values are also set forth in Table 6 above. The viscosities and pH values were suitable for liquid makeup.

Example 11

A. Process For Preparing Hydroxylated Milk Glyceride

To a 2,000 gallon reactor, 6515 pounds of milk fat (obtained from Land O'Lakes, Inc., Arden Hills, Minn. were added having an Epoxide Value of 0.2, a Hydroxyl Value of 1.8 and Iodine Value of 33.6, or 132 millimoles of ethylenic unsaturation per 100 grams. The milk fat was heated to about 40° C. Then, 1432 pounds of heptane were poured in. The solution was stirred for one-half hour while the temperature was maintained between 35° and 40° C. About 770 pounds of acetic acid were added to this mixture followed by 60 pounds of 51 weight % aqueous solution of sulfuric acid. Over a one-hour period at 45°–50° C., 930 pounds of a 50 weight % aqueous hydrogen peroxide solution were added to the mixture in small increments. The temperature was increased to about 58° to 60° C. and stirred for six hours.

The stirring was then stopped and the solution was allowed to settle. A lower aqueous layer and an upper heptane layer formed. The lower aqueous layer was removed and the upper heptane layer was washed three times with hot water (approx. 60° C.). The washed heptane layer was then neutralized with aqueous sodium carbonate solution to a pH of about 6. The heptane was then removed by distillation under vacuum and the reaction product was dried under vacuum at 100° C. The dried product was steam deodorized under vacuum conditions for three hours, neutralized again to pH 6 and filtered at about 50° to 60° C. using diatomaceous earth. This yielded 6135 pounds of a white, soft solid with a Hydroxyl Value of 33.4, Iodine Value of 1.0 and an Epoxide Value of 40.0. The product has approximately 3.9 millimoles of ethylenic unsaturation/100 grams of material.

B. Oxidation of Milk Fat (Rancidification)

A 500 gram sample of the milk fat raw material used in Example 12 was placed in a 4-necked round bottom flask and maintained at 85° C. with agitation and under an air purge. Aliquot samples we re removed from the flask after 48 hours, 144 hours and 168 hours, respectively. The Iodine Value, Hydroxyl Value and Epoxide Value of each sample were measured and are reported in the following Table 10. (The values for the milk fat raw material and hydroxylated milk fat from Example 11A are also reported.)

TABLE 10

| Sample | Iodine Value | Hydroxyl Value | Epoxide Value |
| --- | --- | --- | --- |
| Milk Fat | 33.6 | 1.8 | 0.2 |
| Hydroxylated Milk Fat | 1.0 | 33.4 | 40.0 |
| Oxidized Milk Fat (rancid) | | | |
| (t = 48 hrs) | 34.1 | 3.8 | 0.2 |
| (t = 144 hrs) | 21.9 | 15.0 | 7.9 |
| (t = 168 hrs) | 18.6 | 19.1 | 10.1 |

The data from Table 10 show that the hydroxylated milk fat had an Iodine Value of 1.0, whereas the oxidized milk fat samples retained high Iodine Values indicating a relatively high level of unsaturation. Also, the Hydroxyl Value of the hydroxylated milk fat was 33.4 which was significantly higher than the oxidized samples which ranged from 3.8 to 19.1. Similarly, the Epoxide Value of the hydroxylated milk fat was 40.0 versus values of 0.2 to 10.1 for the oxidized material. Furthermore, the oxidized samples had a very unpleasant odor which is characteristic of rancid milk fat whereas the hydroxylated milk fat had no unpleasant odor. The Saponification Values (also determined in accordance the method referenced in the application) for the raw material milk fat, hydroxylated milk fat and oxidized milk fat samples ranged from 224 to 248. The data shown above demonstrate that the hydroxylated milk fat of the present invention is not the same as the oxidized milk fat of the cited reference and thus novel over oxidized, i.e., rancid, milk fat.

The above examples demonstrate quite surprisingly that, in addition to providing resistance to rancidification, personal care compositions comprising the hydroxylated milk glycerides of the present invention had better characteristics than the same personal care compositions either without the hydroxylated milk glycerides or with milk fat instead of the hydroxylated milk glycerides.

Those skilled in the art will recognize that although the invention has been described above with respect to specific aspects, other aspects are intended to be included within the scope of the invention. For example, the milk fat may be adulterated to adjust its properties prior to being used in the present invention, such as, for example, by fractionation or by adding low or high molecular weight fatty acids or acid esters, either saturated or unsaturated. Futhermore, those skilled in the art may find uses for the hydroxylated milk glycerides other than in personal care compositions, such as, for example, in pharmaceuticals, dispersants, thickeners, etc.

We claim:

1. A personal care composition comprising:
   (1) a hydroxylated milk fat composition comprising hydroxylated triglycerides which comprise:
      (a) from about 50 to 90 weight percent carbon;
      (b) from about 5 to 20 weight percent hydrogen; and
      (c) from about 5 to 20 weight percent oxygen; wherein said triglycerides have;
         (i) a melting point of less than about 60° C.;
         (ii) a molecular weight of from about 650 to 775 grams per gram mole; and
         (iii) an infrared absorbence spectrum which has an OH absorption band at a wave number of from about 3600 to 3300 cm$^{-1}$ and a CH$_2$ absorption band at a wave number of from about 740 to 710 cm$^{-1}$;
      the ratio of the area of said OH absorption band to the area of said CH$_2$ absorption band being at least about 10×10$^{-2}$;
         (iv) an Iodine Value of less than 10; and
         (v) an Epoxide Value of greater than 10; and
   (2) a carrier:
   wherein the hydroxylated milk fat composition is present in an amount effective to enhance at least one of the following properties of the composition; after-feel, dispersibility, emolliency, emulsifiability, gloss, lubricity, moisturizing ability, smoothness, emulsion stability, rub-in, pigment wetting and viscosity.

2. The hydroxylated triglycerides of the milk fat composition of claim 1 wherein the ratio of the area said OH absorption band to the area said CH$_2$ absorption band is at least about 30×10$^{-2}$.

3. The hydroxylated triglycerides of the milk fat composition of claim 1 having an OH absorption band at a wave number of about 3470 cm$^{-1}$.

4. The hydroxylated triglycerides of the milk fat composition of claim 1 having an OH absorption band at a wave number of about 3533 cm$^{-1}$.

5. The hydroxylated triglycerides of the milk fat composition of claim 1 having a $CH_2$ absorption band at a wave number of about 721 $cm^{-1}$.

6. The hydroxylated triglycerides of the milk fat composition of claim 1 which have a melting point of about 20° to 50° C.

7. A hydroxylated milk fat composition comprising hydroxylated triglycerides which upon hydrolysis yields:

(i) glycerol; and (ii) a fatty acid portion comprising:

(a) from about 1 to 10 weight percent of fatty acids containing from 4 to 8 carbon atoms;

(b) from about 5 to 30 weight percent of fatty acids containing from 9 to 14 carbon atoms; and (c) from about 60 to 94 weight percent of fatty acids containing from 15 to 20 carbon atoms, wherein at least 10 weight percent of the fatty acids from groups (a), (b) or (c) contain hydroxyl groups and said triglycerides have;

(1) an Iodine Value of less than 10; and (2) an Epoxide Value of greater than 10.

8. The hydroxylated triglycerides of the milk fat composition of claim 7 which have a Hydroxyl Value of greater than 10.

9. The hydroxylated triglycerides of the milk fat composition of claim 7 having an Iodine Value of from about 0.1 to 2.0.

10. A personal care composition comprising the composition of claim 7 and a carrier wherein the hydroxylated milk fat composition is present in an amount effective to enhance at least one of the following properties of the composition; after-feel, dispersibility, emolliency, emulsifiability, gloss, lubricity, moisturizing ability, smoothness, emulsion stability, rub-in, pigment wetting and viscosity.

11. The personal care composition of claim 10 wherein the fatty acids of said hydroxylated milk fat composition containing 15 to 20 carbon atoms contain an amount of hydroxyl groups effective to inhibit the rancidification of the hydroxylated derivative when stored at a temperature of from about 15° to 30° C. for at least one month.

12. The personal care composition of claim 10 wherein the concentration of the hydroxylated milk fat composition in the composition is from about 0.1 to 20 weight percent.

13. A hydroxylated milk fat composition comprising hydroxylated triglycerides having the following structure:

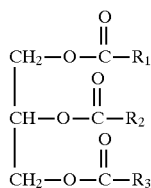

Wherein for each triglyceride;

$R_1$, $R_2$ and $R_3$ substituents may be the same or different and have the formula;

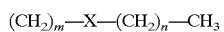

Wherein;

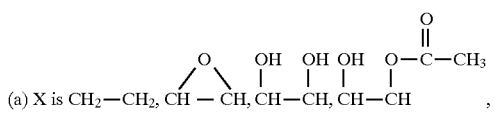

or mixtures thereof;

(b) m is an integer from 0 to about 17; and (c) n is an integer from 0 to about 17;

Provided that on average for the entire composition:

(i) in at least about 1 to 10 weight percent of said $R_1$, $R_2$ or $R_3$ substituents;

(1) X is $CH_2$—$CH_2$, and (2) the sum of m+n is 1 to 5;

(ii) in at least about 5 to 30 weight percent of said $R_1$, $R_2$ or $R_3$ substituents;

(1) X is $CH_2$—$CH_2$, and (2) the sum of m+n is 6 to 11; and (iii) in at least about 60 to 94 weight percent of said $R_1$, $R_2$ or $R_3$ substituents;

(1) at least a portion of said X groups are;

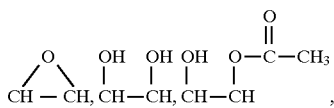

or mixtures thereof; and (2) the sum of m+n is 12 to 17; and

Wherein said triglycerides have:

(a) an Iodine Value of less than 10;

(b) an Epoxide Value of greater than 10.

14. The hydroxylated milk fat composition of claim 13 wherein the portion of X groups which are

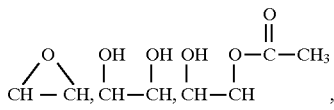

is from about 10 to 100 weight percent of the X groups in the substituents of claim 13(iii).

15. The hydroxylated milk fat composition of claim 13 wherein the portion of X groups which are

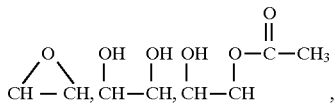

is from about 50 to 100 weight percent of the X groups in the substituents of claim 13(iii).

16. The hydroxylated milk fat composition of claim 13 wherein the portion of X groups which are

is from about 30 to 100 weight percent of the X groups in the substituents of claim 13(iii).

17. The hydroxylated milk fat composition of claim 13 wherein the molar ratio of X groups having the formula

to X groups having the formula

is from about 0.05:1 to 30:1.

18. The hydroxylated milk fat composition of claim 13 wherein the milk fat is obtained from cow's milk or butter.

19. A personal care composition comprising:
   (A) a hydroxylated milk fat composition comprising triglycerides which upon hydrolysis yields:
      (i) glycerol; and
      (ii) a fatty acid portion comprising:
         (a) from about 1 to 10 weight percent of fatty acids containing from 4 to 8 carbon atoms;
         (b) from about 5 to 30 weight percent of fatty acids containing from 9 to 14 carbon atoms; and
         (c) from about 60 to 94 weight percent of fatty acids containing from 15 to 20 carbon atoms, wherein at least 10 weight percent of the fatty acids from groups (a), (b) or (c) contain hydroxyl groups and said triglycerides have
            (1) an Iodine Value of less than 10;
            (2) an Epoxide Value of greater than 10; and
   (B) a carrier:
   wherein the hydroxylated milk fat composition is present in an amount effective to enhance at least one of the following properties of the composition; after-feel, dispersibility, emolliency, emulsifiability, gloss, lubricity, moisturizing ability, smoothness, emulsion stability, rub-in, pigment wetting and viscosity.

20. An hydroxylated milk fat composition comprising triglycerides having an Iodine Value of less than 10, an Epoxide Value of greater than 10 and a Saponification Value of at least about 210.

21. The composition of claim 20 wherein the Iodine Value of triglycerides is less than 5.

22. The composition of claim 20 wherein the Iodine Value of triglycerides is from about 0.1 to 2.0.

23. The composition of claim 20 wherein the triglycerides have a Hydroxyl Value of greater than 10.

24. The composition of claim 20 wherein the triglycerides have a Hydroxyl Value of greater than 20.

25. The composition of claim 20 wherein the Epoxide Value of the triglycerides is from about 25 to 65.

26. The composition of claim 20 wherein the Saponification Value of the triglycerides is from about 210 to 245.

* * * * *